US012178577B2

(12) United States Patent
Liu

(10) Patent No.: US 12,178,577 B2
(45) Date of Patent: Dec. 31, 2024

(54) METHOD AND APPARATUS FOR FATIGUE PREDICTION BASED ON ANALOGUE BRAIN WAVE DATA

(71) Applicant: Minjiang University, Fuzhou (CN)

(72) Inventor: Tianjian Liu, Fuzhou (CN)

(73) Assignee: MINJIANG UNIVERSITY, Fuzhou (CN)

( * ) Notice: Subject to any disclaimer, the term of this patent is extended or adjusted under 35 U.S.C. 154(b) by 827 days.

(21) Appl. No.: 17/346,852

(22) Filed: Jun. 14, 2021

(65) Prior Publication Data

US 2021/0393183 A1 Dec. 23, 2021

(30) Foreign Application Priority Data

Jun. 18, 2020 (CN) .......................... 202010561115.3

(51) Int. Cl.
A61B 5/16 (2006.01)
G06T 7/00 (2017.01)

(52) U.S. Cl.
CPC ............ *A61B 5/168* (2013.01); *G06T 7/0012* (2013.01); *G06T 2207/20081* (2013.01); *G06T 2207/20084* (2013.01); *G06T 2207/30016* (2013.01); *G06T 2207/30041* (2013.01)

(58) Field of Classification Search
CPC ....... A61B 5/168; A61B 5/369; A61B 5/7267; A61B 5/18; G06T 7/0012; G06T 2207/20081; G06T 2207/20084; G06T 2207/30016; G06T 2207/30041; G06T 2207/10016; G08B 21/06; G06F 18/214; G06V 40/171; G06V 40/18
See application file for complete search history.

(56) References Cited

U.S. PATENT DOCUMENTS

2019/0180448 A1* 6/2019 Ro .......................... G06V 40/20
2020/0104616 A1* 4/2020 el Kaliouby ........... A61B 5/163
2020/0293833 A1* 9/2020 Luo ........................ G06N 3/047

* cited by examiner

*Primary Examiner* — Akwasi M Sarpong
*Assistant Examiner* — Michael L Burleson
(74) *Attorney, Agent, or Firm* — Ming Jiang; MM IP SERVICES LLC

(57) ABSTRACT

The present disclosure discloses methods and apparatus for fatigue prediction based on analogue brain wave data, wherein one of the methods comprises: collecting an eye video sequence based on a video capture device; inputting the eye video sequence into a default fatigue discriminator to obtain predicted analogue brain wave data; and outputting the analogue brain wave data to a fatigue discriminant to discriminate a fatigue state. By adopting such a method for fatigue prediction based on analogue brain wave data described in the present disclosure, corresponding analogue brain wave data can be generated through acquiring eye image data, and the fatigue state can be predicted according to the analogue brain waves, so as to avoid tedious operation steps and improve the robustness and accuracy of the fatigue state detection, thereby greatly improving the user experience.

8 Claims, 7 Drawing Sheets

Eye image capture unit 201

Analogue brain wave data acquisition unit 202

Fatigue state discrimination unit 203

FIG. 2

METHOD AND APPARATUS FOR FATIGUE PREDICTION BASED ON ANALOGUE BRAIN WAVE DATA

CROSS REFERENCE TO RELATED APPLICATIONS

This patent application claims the benefit and priority of Chinese Patent Application No. 202010561115.3, filed on Jun. 18, 2020, the disclosure of which is incorporated by reference herein in its entirety as part of the present application.

TECHNICAL FIELD

Embodiments of the present disclosure relate to the technical field of artificial intelligence, and in particular to a method and an apparatus for fatigue prediction based on analogue brain wave data, as well as a storage medium readable to electronic devices and computers.

BACKGROUND ART

With the rapid development of economy and society in recent years, people are suffering from increasing work pressure and life pressure, and most people are subjected to tension fatigue, mental fatigue or sport fatigue to different extents. Fatigue influences people's ability to live or work normally, and will have a negative impact on people's alertness, agility, coordination of actions, information processing and decision-making abilities, and even bring severe threats to people's lives and property, such as traffic accidents caused by fatigue driving. Therefore, the way of timely and effective detection and early warning of the fatigue state based on portable equipment has become a research focus of technicians in this art.

In order to solve the above-mentioned technical problems, methods in the prior art for detecting the fatigue state mainly include determining recent attention concentration of a testee and whether his/her whole body feels weak according to collected eye image features of the testee; or directly acquiring real brain wave data of the testee through brain wave detection equipment so as to make further discrimination. However, when these two methods are used to detect the fatigue state of the testee, either the detection result is not accurate enough, or the detection process to be implemented is too cumbersome, and not well suited to portable detection equipment. As a result, they cannot effectively meet practical needs of users.

SUMMARY

Therefore, embodiments of the present disclosure provide a method for fatigue prediction based on analogue brain wave data to solve problems of complicated methods and equipment for fatigue state detection, low accuracy, and thus relatively poor user experiences in the prior art.

In order to achieve the above purpose, embodiments in the present disclosure provide the following technical scheme:

In a first aspect, an embodiment of the present disclosure provides a method for fatigue prediction based on analogue brain wave data, including: collecting an eye video sequence based on a video capture device; inputting the eye video sequence into a default fatigue discriminator to obtain predicted analogue brain wave data; and outputting the analogue brain wave data to a fatigue discriminator to discriminate a fatigue state.

Further, the method for fatigue prediction based on analogue brain wave data also includes: extracting an eye video sequence when the testee is awake and corresponding brain wave data in an awake state, an eye video sequence when the testee is fatigued and corresponding brain wave data in a fatigue state as training sample data, training a preset generative adversarial network, and adjusting parameters to obtain a target generative adversarial network; wherein the target generative adversarial network includes a generator model, an evaluator model, an adversarial discriminator and the above-mentioned fatigue discriminator; and obtaining the fatigue discriminator from the target adversarial network model.

Further, the step of extracting the eye video sequence when the testee is awake and corresponding brain wave data in the awake state, the eye video sequence when the testee is fatigued and corresponding brain wave data in the fatigue state as training sample data, training the preset generative adversarial network, and adjusting parameters to obtain the target generative adversarial network specifically includes:

Acquiring the eye video sequence when the testee is awake and brain wave data when the testee is fatigued; according to the eye video sequence in the awake state and the brain wave data in the fatigue state, acquiring a composite eye video sequence in the fatigue state; inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

Inputting the composite eye video sequence in the fatigue state and the original eye video sequence in the fatigue state into the evaluator model for evaluation and analysis to obtain perception loss data;

Inputting the composite eye video sequence in the fatigue state into the fatigue discriminator to obtain detected brain wave data; and comparing and analyzing the detected brain wave data with the brain wave data in the fatigue state to obtain detection loss data;

Adjusting parameters of an initial adversarial network model according to the reconstruction loss data, the perception loss data and the detection loss data to obtain the target adversarial network model.

Further, the method for fatigue prediction based on analogue brain wave data also includes: inputting the composite eye video sequence in the fatigue state into the adversarial discriminator to obtain true or false information; obtaining adversarial loss data according to the true or false information; and adjusting parameters of an initial adversarial network model according to the adversarial loss data, the reconstruction loss data, the perception loss data and the detection loss data to obtain the target adversarial network model.

Further, the method for fatigue prediction based on analogue brain wave data also includes: in the training process, expanding the brain wave data to a same size as that of an eye video sequence image, and using each piece of one-dimensional brain wave data as a channel for composition with the eye video sequence image; wherein the brain wave data includes brain wave data when the testee is fatigued and brain wave data when the testee is awake.

In a second aspect, an embodiment of the present disclosure also provides an apparatus for fatigue prediction based on analogue brain wave data, including: an eye image capture unit, used for collecting an eye video sequence based on a video capture device; an analogue brain wave data acquisition unit, used for inputting the eye video sequence into a default fatigue discriminator to obtain predicted analogue brain wave data; and a fatigue state discrimination unit, used for outputting the analogue brain wave data to a fatigue discriminant to discriminate a fatigue state.

Further, the apparatus for fatigue prediction based on analogue brain wave data also includes: a training unit, used for extracting an eye video sequence when the testee is awake and corresponding brain wave data in an awake state, an eye video sequence when the testee is fatigue and corresponding brain wave data in a fatigue state as training sample data, training a preset generative adversarial network, and adjusting parameters to obtain a target generative adversarial network; wherein the target generative adversarial network includes a generator model, an evaluator model, an adversarial discriminator and the above-mentioned fatigue discriminator; and a fatigue discriminator acquisition unit, used for obtaining the fatigue discriminator from the target adversarial network model.

Further, the training unit is specifically used for:

Acquiring the eye video sequence when the testee is awake and brain wave data when the testee is fatigued; according to the eye video sequence in the awake state and the brain wave data in the fatigue state, acquiring a composite eye video sequence in the fatigue state; inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

Inputting the composite eye video sequence in the fatigue state and the original eye video sequence in the fatigue state into the evaluator model for evaluation and analysis to obtain perception loss data;

Inputting the composite eye video sequence in the fatigue state into the fatigue discriminator to obtain detected brain wave data; and comparing and analyzing the detected brain wave data with the brain wave data in the fatigue state to obtain detection loss data;

Adjusting parameters of an initial adversarial network model according to the reconstruction loss data, the perception loss data and the detection loss data to obtain the target adversarial network model.

Further, the apparatus for fatigue prediction based on analogue brain wave data also includes: an adversarial loss data acquisition unit, used for inputting the composite eye video sequence in the fatigue state into the adversarial discriminator to obtain true or false information; obtaining adversarial loss data according to the true or false information; and a target adversarial network model acquisition unit, used for adjusting parameters of an initial adversarial network model according to the adversarial loss data, the reconstruction loss data, the perception loss data and the detection loss data to obtain the target adversarial network model.

Further, the apparatus for fatigue prediction based on analogue brain wave data also includes: a parameter adjustment unit, used in the training process for expanding the brain wave data to a same size as that of an eye video sequence image, and using each piece of one-dimensional brain wave data as a channel for composition with the eye video sequence image; wherein the brain wave data includes brain wave data when the tester is fatigued and brain wave data when the tester is awake.

In a third aspect, an embodiment of the present disclosure also provides a training method of generative adversarial network, including: acquiring the eye video sequence when the testee is awake and brain wave data when the testee is fatigued; according to the eye video sequence in the awake state and the brain wave data in the fatigue state, acquiring a composite eye video sequence in the fatigue state; inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data; inputting the composite eye video sequence in the fatigue state and the original eye video sequence in the fatigue state into the evaluator model for evaluation and analysis to obtain perception loss data; inputting the composite eye video sequence in the fatigue state into the fatigue discriminator to obtain detected brain wave data; and comparing and analyzing the detected brain wave data with the brain wave data in the fatigue state to obtain detection loss data; and adjusting parameters of the initial adversarial network model according to the reconstruction loss data, the perception loss data and the detection loss data to obtain the target adversarial network model.

In a fourth aspect, an embodiment of the present disclosure also provides a training apparatus of generative adversarial network, including: a composition processing unit, used for acquiring the eye video sequence when the testee is awake and brain wave data when the testee is fatigued; according to the eye video sequence in the awake state and the brain wave data in the fatigue state, acquiring a composite eye video sequence in the fatigue state; a reconstruction processing unit, used for inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data; an evaluation and analysis unit, used for inputting the composite eye video sequence in the fatigue state and the original eye video sequence in the fatigue state into the evaluator model for evaluation and analysis to obtain perception loss data; a brain wave detection and analysis unit, used for inputting the composite eye video sequence in the fatigue state into the fatigue discriminator to obtain detected brain wave data; and comparing and analyzing the detected brain wave data with the brain wave data in the fatigue state to obtain detection loss data; and an adjustment unit, used for adjusting parameters of the initial adversarial network model according to the reconstruction loss data, the perception loss data and the detection loss data to obtain the target adversarial network model.

In a fifth aspect, an embodiment of the present disclosure also provides an electronic device, including: a processor and a memory; wherein the memory is used for storing a program of the method for fatigue prediction based on analogue brain wave data; after the electronic device is powered on and the processor runs the program of the method for fatigue prediction based on analogue brain wave data, the electronic device performs the method for fatigue prediction based on analogue brain wave data described in any above-mentioned aspect.

In a sixth aspect, an embodiment of the present disclosure also provides a computer-readable storage medium, wherein the computer storage medium includes one or more program instructions, and the one or more program instructions are used by the processor to perform the method for fatigue prediction based on analogue brain wave data described in any above-mentioned aspect.

By adopting the method for fatigue prediction based on analogue brain wave data described in the present disclosure, corresponding analogue brain wave data can be generated through acquiring eye image data, and the fatigue state can be predicted according to the analogue brain waves, so as to avoid tedious operation steps and improve the robustness and accuracy of the fatigue state detection, thereby effectively improving the user experience.

By adopting the training method of generative adversarial network, realistic composite data can be generated through limited experimental data, so as to expand a limited training data set and fix the problem of low fatigue state detection accuracy in practice due to insufficient training data. Besides, the adversarial training method can improve the robustness, accuracy and generalization ability of the fatigue detection discriminator.

BRIEF DESCRIPTION OF THE DRAWINGS

In order to illustrate the implementations of the present disclosure more clearly, the accompanying drawings required in the implementations or prior art will be briefly introduced below. Apparently, the drawings in the following description are only illustrative, and those of ordinary skills in the art may derive other implementation drawings according to these drawings provided herein without creative work.

FIG. 2 is a schematic diagram of an apparatus for fatigue prediction based on analogue brain wave data provided in embodiments of the present disclosure;

DETAILED DESCRIPTION OF THE EMBODIMENTS

Implementations of the present disclosure will be illustrated through specific embodiments below. Those skilled in the art can easily understand other advantages and effects of the present disclosure from the contents disclosed in this specification. Obviously, the described embodiments are part of, but not all of, the embodiments of the present disclosure. Based on the embodiments of the present disclosure, all other embodiments obtained by those of ordinary skills in the art without creative work belong to the scope claimed by the present disclosure.

Figure 1:
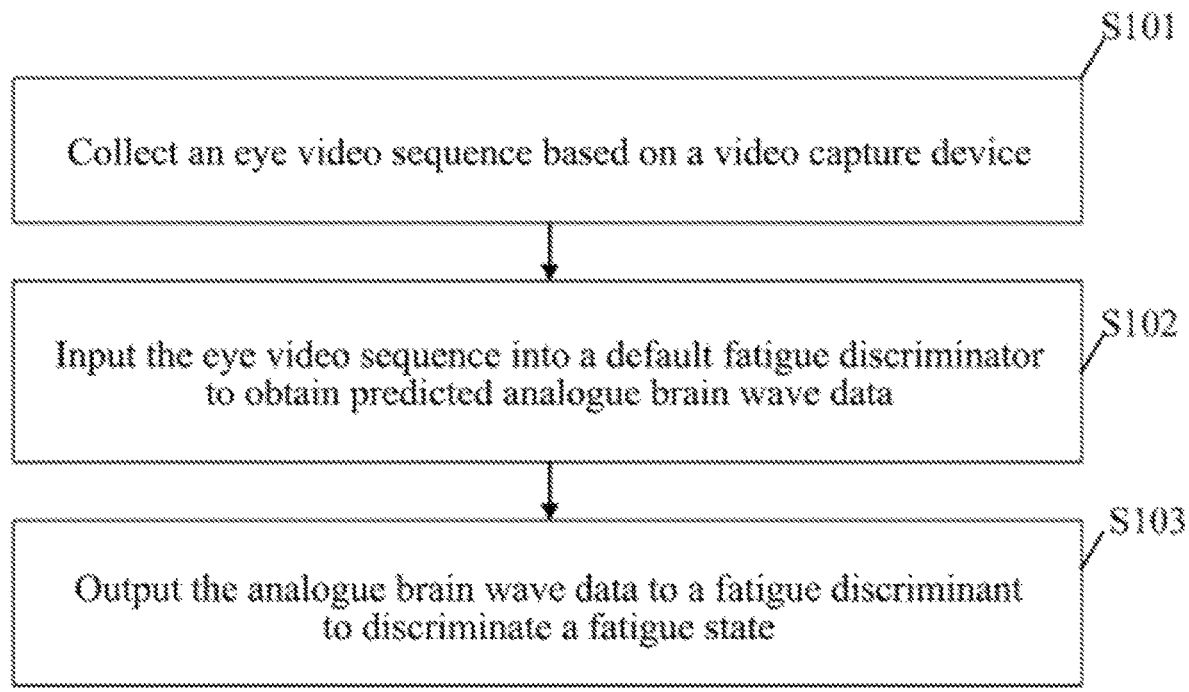
FIG. 1 is a flow chart of a method for fatigue prediction based on analogue brain wave data provided in embodiments of the present disclosure.

According to the method for fatigue prediction based on analogue brain wave data described in the present disclosure, the embodiments of the method will be described in detail below. As shown in FIG. 1, FIG. 1 is a flowchart of a method for fatigue prediction based on analogue brain wave data provided in embodiments of the present disclosure, the specific implementation of which includes:

Step 101: collecting an eye video sequence based on a video capture device.

In this embodiment of the present disclosure, the video capture device may refer to a small camera and the like, and the eye video sequence refers to a sequence of several video frame images containing the eyes in a collected piece of video data.

Figure 7:
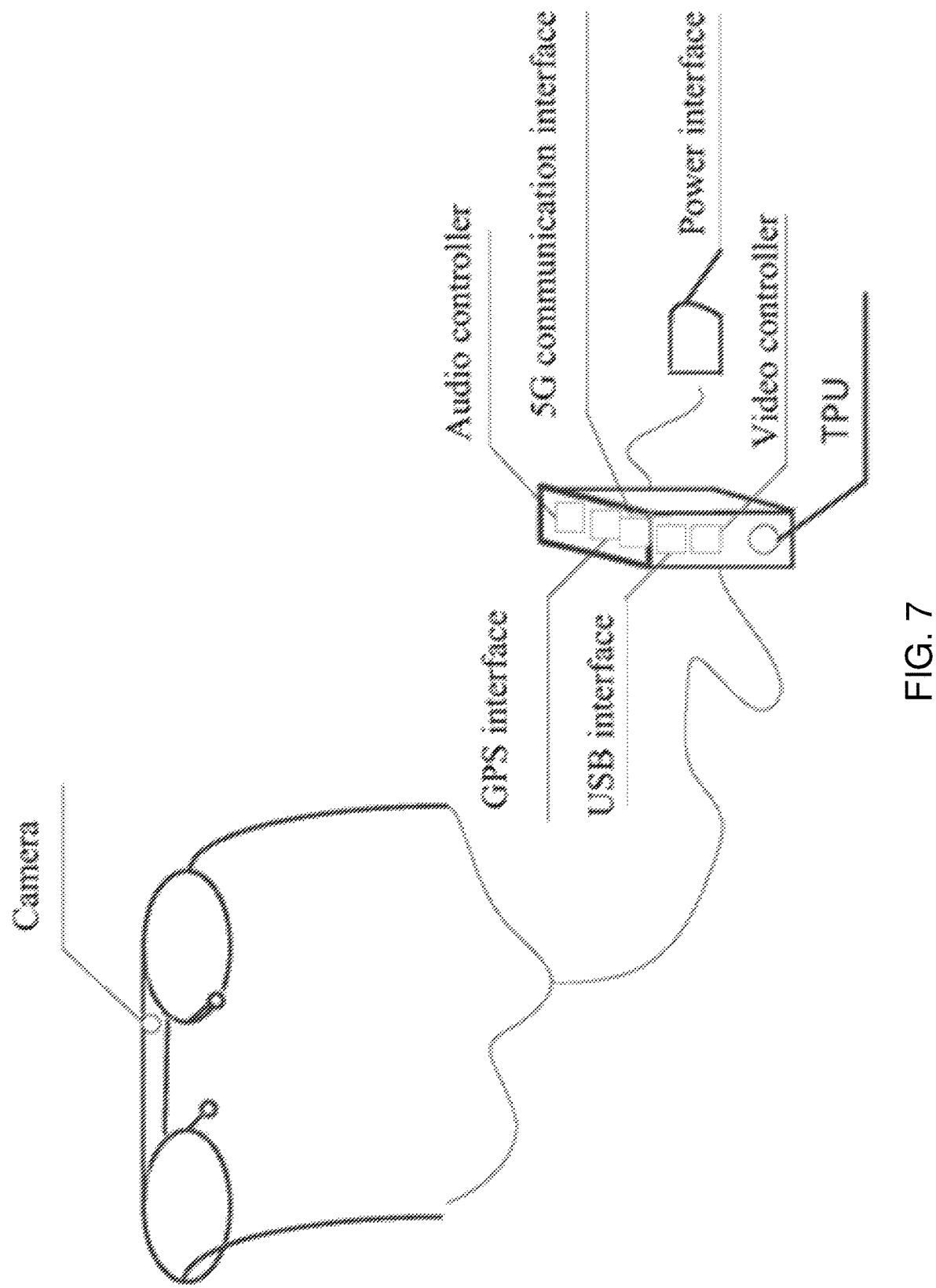
FIG. 7 is a structural schematic diagram of a wearable fatigue-warning electronic device based on analogue brain wave provided in embodiments of the present disclosure.

At present, the non-contact video fatigue detection apparatus has two ways of data collection, which include collecting facial information through a remote camera and collecting eye information at close range through a portable wearable device. By using a remote fatigue detection apparatus, the camera has a wider field of view so that it only collects limited facial information and is susceptible to the environment, which affects the accuracy of fatigue discrimination. Instead, with a fatigue detection apparatus of portable wearable devices, the camera collects rich eye image information that shows a strong correlation between the eye state and the fatigue. Therefore, in an implementation of the present disclosure, the video capture device is preferentially installed on a portable wearable device such as glasses (as shown in FIG. 7) and a helmet to capture an eye video sequence at close range.

Step 102: inputting the eye video sequence into a default fatigue discriminator to obtain predicted analogue brain wave data.

After collection of the eye video sequence in Step 101, in this step the eye video sequence is input into a fatigue discriminator well trained in advance, so as to obtain predicted analogue brain wave data.

In an embodiment of the present disclosure, it is required to extract in advance: the eye video sequence when the testee is awake and corresponding brain wave data in the awake state, the eye video sequence when the testee is fatigued and corresponding brain wave data in the fatigue state as training sample data, training the preset generative adversarial network, and adjusting parameters to obtain the target generative adversarial network; wherein the target generative adversarial network includes a generator model, an evaluator model, and a discriminator model, wherein the discriminator model consists of an adversarial discriminator and the above-mentioned fatigue discriminator. After the training and parameter adjustment to obtain the target generative adversarial network, the fatigue discriminator used for fatigue state detection may be further obtained from the target adversarial network model.

In the step of extracting the eye video sequence when the testee is awake and corresponding brain wave data in the awake state, the eye video sequence when the testee is fatigued and corresponding brain wave data in the fatigue state are used as training sample data to train the preset generative adversarial network and adjust parameters, so as to obtain the target generative adversarial network, the specific implementation of which may include:

Firstly, acquiring the eye video sequence when the testee is awake and brain wave data when the testee, is fatigued; and according to the eye video sequence in the awake state and the brain wave data in the fatigue state, acquiring a composite eye video sequence in the fatigue state;

Secondly, inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data; besides, inputting the composite eye video sequence in the fatigue state and the original eye video sequence in the fatigue state into the evaluator model for evaluation and analysis to obtain perception loss data; and inputting the composite eye video sequence in the fatigue state into the fatigue discriminator to obtain detected brain wave data; and comparing and analyzing the detected brain wave data with the brain wave data in the fatigue state to obtain detection loss data;

Finally, adjusting parameters of the initial adversarial network model according to the reconstruction loss data, the perception loss data and the detection loss data to obtain the target adversarial network model.

It should be noted that in the training process, the brain wave data is expanded to a same size as that of an eye video sequence image, and each piece of one-dimensional brain wave data acts as a channel for composition with the eye video sequence image; wherein the brain wave data includes brain wave data when the testee is fatigued and brain wave data when the testee is awake, and correspondingly the eye video sequence image may refer to either the eye video sequence image when the testee, is awake, or the eye video sequence image when the testee is fatigued.

In the practical implementation, the method for fatigue prediction based on analogue brain wave data also includes: inputting the composite eye video sequence in the fatigue state into the adversarial discriminator to obtain true or false information; obtaining adversarial loss data according to the true or false information; and further adjusting parameters of an initial adversarial network model according to the adversarial loss data, the reconstruction loss data, the perception loss data and the detection loss data to obtain the target adversarial network model. It should be noted that the analogue brain wave data described in the present disclosure is brain wave data predicted through eye images, but not real brain wave data directly measured, which enables easier operation of devices and quick acquisition of generated brain wave data which effectively represent the fatigue state of the human body.

Figure 6:
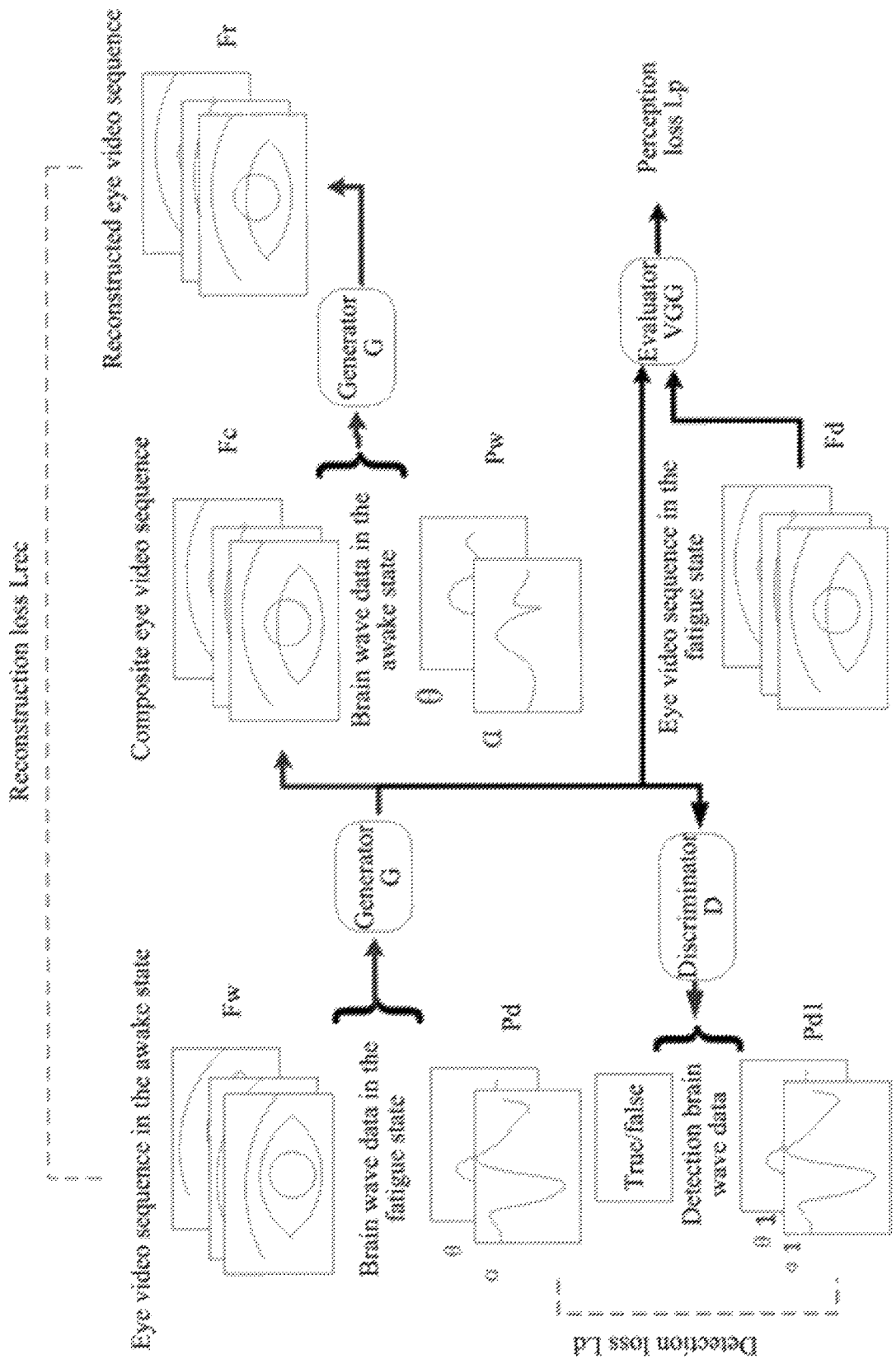
FIG. 6 is a complete flow chart of a training method of a generative adversarial network provided in embodiments of the present disclosure.

As shown in FIG. 6, FIG. 6 is a complete flow chart of a training method of a generative adversarial network provided in embodiments of the present disclosure. The generative adversarial network includes a generator G, a discriminator D, and an evaluator VGG, wherein the discriminator D consists of two parts: an adversarial discriminator Da and a fatigue discriminator Dd.

In the actual implementation, it is necessary to use an improved condition generative adversarial network FatigueNet to detect fatigue in advance, i.e., to extract from the experimental data set an eye video sequence when the testee is awake and corresponding brain wave data in the awake state {Fw, Pw}, an eye video sequence when the tester is fatigued and corresponding brain wave data in the fatigue state {Fd, Pd}, and to input the data into the above-mentioned generative adversarial network for data composition, reconstruction, discrimination, evaluation and detection.

Specifically, the composition process includes: inputting the eye video sequence in the awake state Fw and the brain wave data in the fatigue state Pd to a generator G to generate a composite eye video sequence Fc (i.e., compositing an eye video sequence in the fatigue state). The reconstruction process includes: inputting the composite eye video sequence Fc and the brain wave data in the awake state Pw into the generator G to generate a reconstructed eye video sequence (i.e., a reconstructed eye video sequence in the awake state); comparing and analyzing the reconstructed eye video sequence with the eye video sequence in the awake state to obtain reconstruction loss data Lrec. The discrimination process includes: inputting the composite eye video sequence Fc into a discriminator D, wherein the discriminator D consists of two parts: an adversarial discriminator Da and a fatigue detection discriminator Dd, and the adversarial discriminator Da and the fatigue detection discriminator Dd share a partial network layer; wherein the adversarial discriminator Da outputs true or false information, the fatigue detection discriminator Dd outputs detected brain wave data; and the detected brain wave data is compared and analyzed with the brain wave data in the fatigue state to obtain detection loss data Ld. At the same time, by analyzing the true or false information generated by the adversarial discriminator Da, the adversarial loss data La can be obtained, wherein the true or false information can be represented by 1 or 0 respectively. In addition, the evaluation process includes: inputting the composite eye video sequence Fc and the brain wave data in the fatigue state Pd into the evaluator VGG, comprehensively evaluating and analyzing the composite data, and obtaining perception loss data Lp according to the evaluation analysis result.

By training the discriminator D, it is used for deploying phased fatigue detection, the adversarial loss data La is used to train the generator G and the discriminator Da, the reconstructed data is consistent with the original data as much as possible by means of composite reconstruction, and the reconstruction loss data Lrec is used to train the generator G. The fatigue discriminator Dd is constrained by way of generative adversarial training and regression training, the adversarial loss data La and detection loss data Ld are used to train the discriminator Dd, and the perception loss data Lp is used to measure the similarity of structure and texture and to train the evaluator VGG, so as to output the training that can restrain the generator G. The adversarial loss, reconstruction loss, perception loss and detection loss together constitute the training of the entire fatigue generative adversarial network. The architectures of the generator and the discriminator D can be composed of basic networks, including a convolution network CNN, a fully connected network FC, a cyclic neural network RNN, a residual network ResNet, and a density network DesNet, which will not be described in detail herein.

Step 103: outputting the analogue brain wave data to a fatigue discriminant to discriminate a fatigue state.

After the predicted analogue brain wave data is obtained in Step 102, in this step, the analogue brain wave data may be output to a fatigue discriminant to discriminate a fatigue state.

In the embodiment of the present disclosure, after the analogue brain wave data is output to the fatigue discriminant, if the testee is discriminated in a fatigue state, a fatigue warning information is generated, which will not be described in detail herein. The fatigue discriminant may simply use a brain wave fatigue discriminant existing in the prior art, such as the fatigue discriminant $\beta+\alpha=((1*10-8)(\alpha+\theta)2+0.3(\alpha+\theta)+5100$; wherein the degree of deviation is $M=[(1*10-8)(\alpha+\theta)2+0.3(\alpha+\theta)+5100-(\beta+\alpha)]/(\beta+\alpha)*100\%$. As the fatigue discriminant is known to those skilled in the art, it will not be described in detail herein.

By adopting the method for fatigue prediction based on analogue brain wave data described in the present disclosure, corresponding analogue brain wave data can be generated through acquiring eye image data, and the fatigue state can be predicted according to the analogue brain waves, so as to avoid tedious operation steps and improve the robustness and accuracy of the fatigue state detection, thereby greatly improving the user experience.

Corresponding to the method for fatigue prediction based on analogue brain wave data provided above, the present disclosure also provides an apparatus for fatigue prediction based on analogue brain wave data. Since the embodiment of the apparatus is similar to that of the above-mentioned method, it has a relatively simple description. Please refer to the illustration of the embodiment of the above-mentioned method for similar content. The embodiment described below is only illustrative for the apparatus for fatigue prediction based on analogue brain wave data. As shown in FIG. 2, FIG. 2 is a schematic diagram of an apparatus for fatigue prediction based on analogue brain wave data provided in embodiments of the present disclosure.

An apparatus for fatigue prediction based on analogue brain wave data is described in the present disclosure, which includes:

An eye image capture unit 201, used for collecting an eye video sequence based on a video capture device;

An analogue brain wave data acquisition unit 202, used for inputting the eye video sequence into a default fatigue discriminator to obtain predicted analogue brain wave data;

A fatigue state discrimination unit 203, used for outputting the analogue brain wave data to a fatigue discriminant to discriminate a fatigue state.

By adopting the apparatus for fatigue prediction based on analogue brain wave data described in the present disclosure, corresponding analogue brain wave data can be generated through acquiring eye image data, and the fatigue state can be predicted according to the analogue brain waves, so as to avoid tedious operation steps and improve the robustness and accuracy of the fatigue state detection, thereby greatly improving the user experience.

Figure 3:
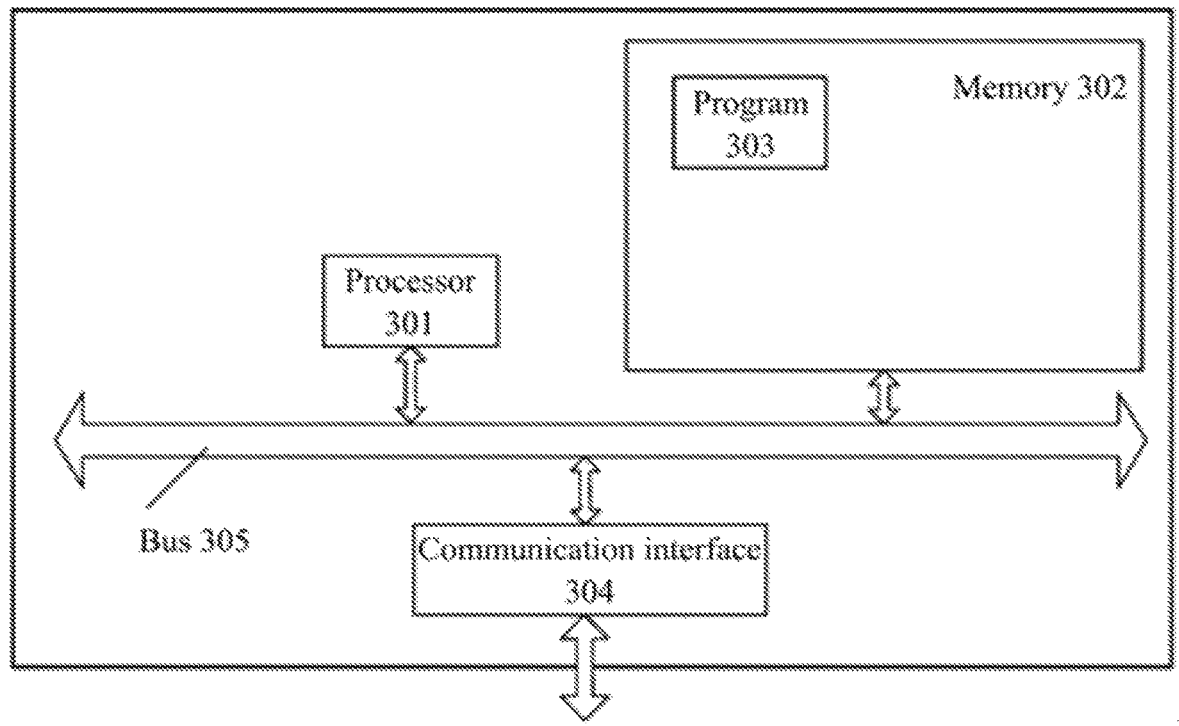
FIG. 3 is a schematic diagram of an electronic device provided in embodiments of the present disclosure.

Corresponding to the method for fatigue prediction based on analogue brain wave data provided above, the present disclosure also provides an electrical device, Since the embodiment of the electrical device is similar to that of the above-mentioned method, it has a relatively simple description. Please refer to the illustration of the embodiment of the above-mentioned method for similar content. The electrical device described below is only for illustration. As shown in FIG. 3, FIG. 3 is a schematic diagram of an electronic device provided in embodiments of the present disclosure. The electronic device specifically includes: a processor 301 and a memory 302; wherein the memory 302 is used for running one or more program instructions and storing a program of the method for fatigue prediction based on analogue brain wave data; after the electronic device is powered on and the processor 301 runs the program of the method for fatigue prediction based on analogue brain wave data, the electronic device performs the method for fatigue prediction based on analogue brain wave data described in any above-mentioned aspect.

Corresponding to the method for fatigue prediction based on analogue brain wave data provided above, the present disclosure also provides a computer-readable storage medium, wherein the computer-readable storage medium comprises one or more program instructions, and the one or more program instructions are used by the processor to perform the method for fatigue prediction based on analogue brain wave data described in any above-mentioned aspect. Since the embodiment of the computer-readable storage medium is similar to the above method embodiment, the description is relatively simple. Please refer to the description of the above method embodiment for relevant points. The computer storage medium described below is only for illustration.

In addition, corresponding to the method for fatigue prediction based on analogue brain wave data provided above, the present disclosure also provides a training method and an apparatus for a generative adversarial network. Since the embodiment of the method and apparatus is similar to that of the above-mentioned method and apparatus for fatigue prediction based on analogue brain wave data, it has a relatively simple description. Please refer to the illustration of the embodiment of the above-mentioned embodiments for similar content. The embodiment described below is only illustrative for the training method and apparatus for the generative adversarial network.

Figure 4:
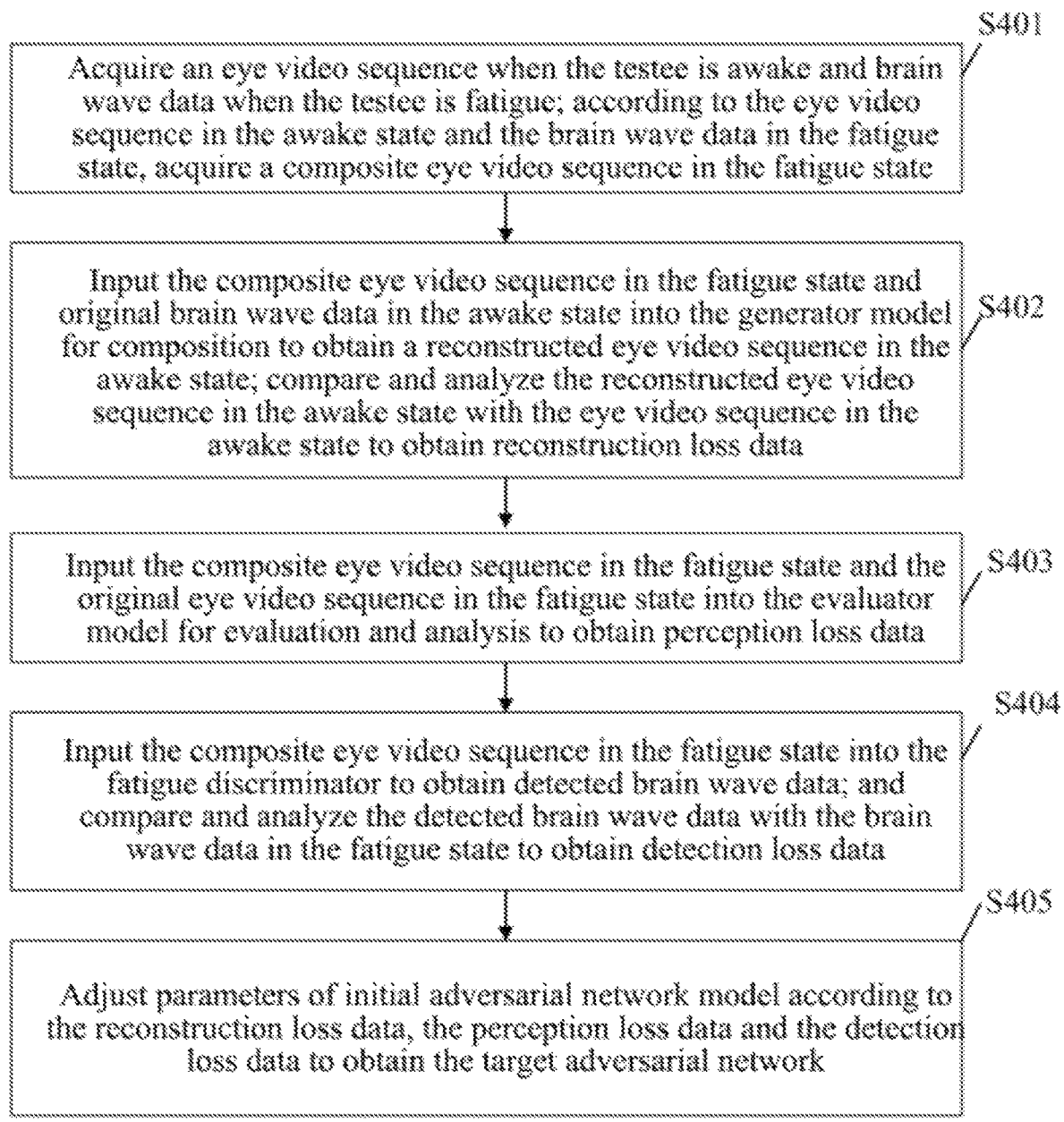
FIG. 4 is a flow chart of a training method of a generative adversarial network provided in embodiments of the present disclosure.

As shown in FIG. 4, FIG. 4 is a flow chart of a training method of a generative adversarial network provided in embodiments of the present disclosure, the specific implementation of which includes:

Step 401: acquiring the eye video sequence when the testee is awake and brain wave data when the testee is fatigued; according to the eye video sequence in the awake state and the brain wave data in the fatigue state, acquiring a composite eye video sequence in the fatigue state;

Step 402: inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

Step 403: inputting the composite eye video sequence in the fatigue state and the original eye video sequence in the fatigue state into the evaluator model for evaluation and analysis to obtain perception loss data;

Step 404: inputting the composite eye video sequence in the fatigue state into the fatigue discriminator to obtain detected brain wave data; and comparing and analyzing the detected brain wave data with the brain wave data in the fatigue state to obtain detection loss data;

Step 405: adjusting parameters of an initial adversarial network model according to the reconstruction loss data, the perception loss data and the detection loss data to obtain the target adversarial network model.

Figure 5:
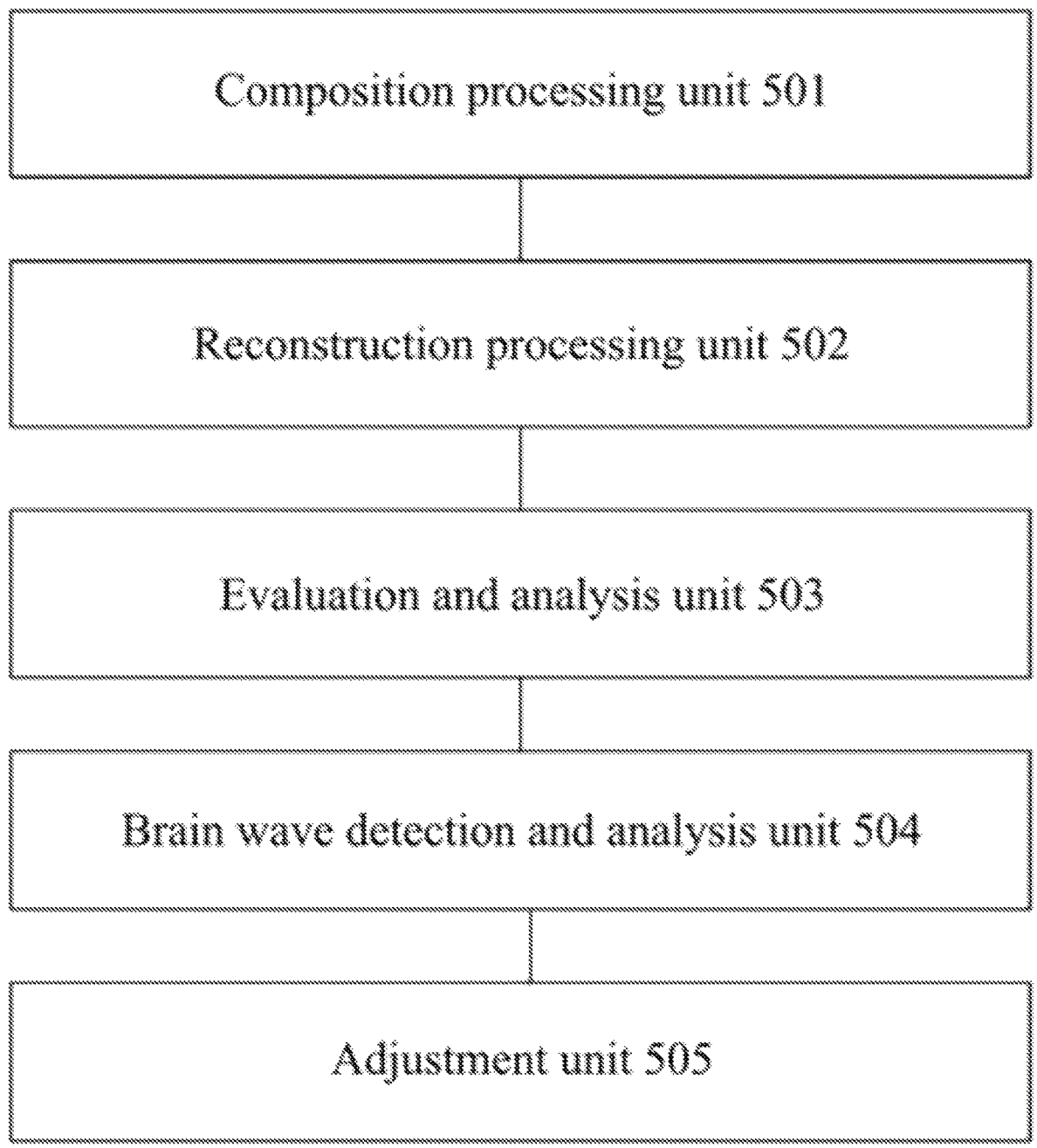
FIG. 5 is a schematic diagram of a training apparatus of a generative adversarial network provided in embodiments of the present disclosure.

As shown in FIG. 5, FIG. 5 is a schematic diagram of a training apparatus of a generative adversarial network provided in embodiments of the present disclosure, the specific implementation of which includes:

A composition processing unit 501, used for acquiring the eye video sequence when the testee is awake and brain wave data when the testee is fatigued; according to the eye video sequence in the awake state and the brain wave data in the fatigue state, acquiring the composite eye video sequence in the fatigue state;

A reconstruction processing unit 502, used for inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

An evaluation and analysis unit 503, used for inputting the composite eye video sequence in the fatigue state and the original eye video sequence in the fatigue state into the evaluator model for evaluation and analysis to obtain perception loss data;

A brain wave detection and analysis unit 504, used for inputting the composite eye video sequence in the fatigue state into the fatigue discriminator to obtain detected brain wave data; and comparing and analyzing the detected brain wave data with the brain wave data in the fatigue state to obtain detection loss data;

An adjustment unit 505, used for adjusting parameters of an initial adversarial network model according to the reconstruction loss data, the perception loss data and the detection loss data to obtain the target adversarial network model.

By adopting the training method and apparatus of the generative adversarial network, realistic composite data can be generated through limited experimental data, so as to expand a limited training data set and fix the problem of low fatigue state detection accuracy in practice due to insufficient training data. Besides, the adversarial training method can improve the robustness, accuracy and generalization ability of the fatigue detection discriminator.

In conclusion, it should be noted that in embodiments of the present disclosure, the processor or processor module may be an integrated circuit chip capable of signal processing. The processor may be a general-purpose processor, a digital signal processor (DSP), an application specific integrated circuit (ASIC), a field programmable gate array (FPGA) or other programmable logic devices, a discrete gate or transistor logic device, a discrete hardware component, and the like.

The processor may implement or perform various methods, steps and logic block diagrams disclosed in embodiments of the present disclosure. A general-purpose processor may be a microprocessor, or this processor may be any conventional processor or the like. The steps of the method disclosed in combination with the embodiment of the present disclosure can be directly embodied as being completed by a hardware decoding processor, or by the combination of hardware and software modules in the decoding processor. The software module can be located in mature storage media in the art such as a random access memory, a flash memory, a read-only memory, a programmable read-only memory, an electrically erasable programmable read-only memory, a register, and the like. The processor reads information in the storage medium and completes the steps of the above-mentioned method in combination with its hardware.

The storage medium may be a memory, for example, a volatile memory or a non-volatile memory, or may include both volatile and non-volatile memories.

Among the memories, a non-volatile memory may be a Read-Only Memory (ROM), a Programmable ROM (PROM), an Erasable PROM (EPROM), an Electrically EPROM (EEPROM), or a flash memory.

A volatile memory may be a Random Access Memory (RAM) which acts as an external high-speed cache. By illustrative but not restrictive illustration, many forms of RAMs are available, for example, a Static RAM (SRAM), a Dynamic RAM (DRAM), a Synchronous DRAM (SDRAM), a Double Data Rate SDRAM (DDRSDRAM), an Enhanced SDRAM (ESDRAM), a Synch link DRAM (SLDRAM), and a Direct Ram bus RAM (DRRAM).

The storage medium described in the embodiment of the present disclosure is intended to include, but not limited to, these and any other suitable types of memories.

Those skilled in the art should realize that in one or more above-mentioned examples, functions described in the present disclosure can be realized by a combination of hardware and software. When software is applied, its corresponding functions can be stored in a computer-readable medium or transmitted as one or more instructions or codes on the computer-readable medium. Computer-readable media include computer storage media and communication media, wherein the communication media include any medium that facilitates the transmission of computer programs from one place to another. The storage media can be any available media that can be accessed by a general-purpose or special-purpose computer.

The specific implementations above further illustrate the purposes, technical schemes and beneficial effects of the present disclosure. It is noted that the above description is intended to describe implementations of the present disclosure without the scope of the present disclosure. Any modification, equivalent replacement, improvement and the like based on the technical scheme of the present disclosure shall be included in the scope of the present disclosure.

What is claimed is:

1. A method for fatigue prediction based on analogue brain wave data, comprising:
    extracting an eye video sequence when the testee is awake and corresponding brain wave data in an awake state, an eye video sequence when the testee is fatigued and corresponding brain wave data in a fatigue state as training sample data;
    training a preset generative adversarial network, and adjusting parameters to obtain a target generative adversarial network; wherein the target generative adversarial network includes a generator model, an evaluator model, an adversarial discriminator and the fatigue discriminator;
    obtaining the fatigue discriminator from the target adversarial network model;
    collecting an eye video sequence based on a video capture device;
    inputting the eye video sequence into a default fatigue discriminator to obtain predicted analogue brain wave data; and
    outputting the analogue brain wave data to the fatigue discriminator to discriminate a fatigue state.

2. The method for fatigue prediction based on analogue brain wave data according to claim 1, comprising:
    extracting an eye video sequence when the testee is awake and corresponding brain wave data in an awake state, an eye video sequence when the testee is fatigued and corresponding brain wave data in a fatigue state as training sample data, training a preset generative adversarial network, and adjusting parameters to obtain a target generative adversarial network, which comprises:
    acquiring the eye video sequence when the testee is awake and brain wave data when the testee is fatigued; according to the eye video sequence in the awake state and the brain wave data in the fatigue state, acquiring a composite eye video sequence in the fatigue state; inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

inputting the composite eye video sequence in the fatigue state and the original eye video sequence in the fatigue state into the evaluator model for evaluation and analysis to obtain perception loss data;

Inputting the composite eye video sequence in the fatigue state into the fatigue discriminator to obtain detected brain wave data; and comparing and analyzing the detected brain wave data with the brain wave data in the fatigue state to obtain detection loss data;

adjusting parameters of an initial adversarial network model according to the reconstruction loss data, the perception loss data and the detection loss data to obtain the target adversarial network model.

3. The method for fatigue prediction based on analogue brain wave data according to claim 2, further comprising:

inputting the composite eye video sequence in the fatigue state into the adversarial discriminator to obtain true or false information;

obtaining adversarial loss data according to the true or false information;

adjusting parameters of an initial adversarial network model according to the adversarial loss data, the reconstruction loss data, the perception loss data and the detection loss data to obtain the target adversarial network model.

4. The method for fatigue prediction based on analogue brain wave data according to claim 2, further comprising:

in the training process, expanding the brain wave data to a same size as that of an eye video sequence image, and using each piece of one-dimensional brain wave data as a channel for composition with the eye video sequence image; wherein the brain wave data includes brain wave data when the testee is fatigued and brain wave data when the testee is awake.

5. An electronic device, comprising:

a processor; and a memory, used for storing a program of a method for fatigue prediction based on analogue brain wave data; after the electronic device is powered on and the processor runs the program of the method for fatigue prediction based on analogue brain wave data, the electronic device performs a method for fatigue prediction based on analogue brain wave data; the method comprises:

extracting an eye video sequence when the testee is awake and corresponding brain wave data in an awake state, an eye video sequence when the testee is fatigued and corresponding brain wave data in a fatigue state as training sample data;

training a preset generative adversarial network, and adjusting parameters to obtain a target generative adversarial network; wherein the target generative adversarial network includes a generator model, an evaluator model, an adversarial discriminator and the fatigue discriminator;

obtaining the fatigue discriminator from the target adversarial network model;

collecting an eye video sequence based on a video capture device;

inputting the eye video sequence into a default fatigue discriminator to obtain predicted analogue brain wave data; and outputting the analogue brain wave data to the fatigue discriminator to discriminate a fatigue state.

6. The electronic device according to claim 5, comprising:

extracting an eye video sequence when the testee is awake and corresponding brain wave data in an awake state, an eye video sequence when the testee is fatigued and corresponding brain wave data in a fatigue state as training sample data, training a preset generative adversarial network, and adjusting parameters to obtain a target generative adversarial network, which comprises:

acquiring the eye video sequence when the testee is awake and brain wave data when the testee is fatigued; according to the eye video sequence in the awake state and the brain wave data in the fatigue state, acquiring a composite eye video sequence in the fatigue state; inputting the composite eye video sequence in the fatigue state and original brain wave data in the awake state into the generator model for composition to obtain a reconstructed eye video sequence in the awake state; comparing and analyzing the reconstructed eye video sequence in the awake state with the eye video sequence in the awake state to obtain reconstruction loss data;

inputting the composite eye video sequence in the fatigue state and the original eye video sequence in the fatigue state into the evaluator model for evaluation and analysis to obtain perception loss data;

inputting the composite eye video sequence in the fatigue state into the fatigue discriminator to obtain detected brain wave data; and comparing and analyzing the detected brain wave data with the brain wave data in the fatigue state to obtain detection loss data;

adjusting parameters of an initial adversarial network model according to the reconstruction loss data, the perception loss data and the detection loss data to obtain the target adversarial network model.

7. The electronic device according to claim 6, further comprising:

inputting the composite eye video sequence in the fatigue state into the adversarial discriminator to obtain true or false information;

obtaining adversarial loss data according to the true or false information; and adjusting parameters of an initial adversarial network model according to the adversarial loss data, the reconstruction loss data, the perception loss data and the detection loss data to obtain the target adversarial network model.

8. The electronic device according to claim 6, further comprising:

in the training process, expanding the brain wave data to a same size as that of an eye video sequence image, and using each piece of one-dimensional brain wave data as a channel for composition with the eye video sequence image; wherein the brain wave data includes brain wave data when the testee is fatigued and brain wave data when the testee is awake.

* * * * *